(12) United States Patent
Lee

(10) Patent No.: US 9,750,335 B2
(45) Date of Patent: Sep. 5, 2017

(54) PORTABLE INTERDENTAL TOOTHBRUSH

(71) Applicant: Sang Geun Lee, Gwangju-si (KR)

(72) Inventor: Sang Geun Lee, Gwangju-si (KR)

( * ) Notice: Subject to any disclaimer, the term of this patent is extended or adjusted under 35 U.S.C. 154(b) by 0 days.

(21) Appl. No.: 14/903,281

(22) PCT Filed: Jul. 17, 2014

(86) PCT No.: PCT/KR2014/006487
§ 371 (c)(1),
(2) Date: Jan. 6, 2016

(87) PCT Pub. No.: WO2016/010176
PCT Pub. Date: Jan. 21, 2016

(65) Prior Publication Data
US 2017/0127817 A1 May 11, 2017

(30) Foreign Application Priority Data

Jul. 17, 2014 (KR) .................. 10-2014-0090113

(51) Int. Cl.
| A61C 15/00 | (2006.01) |
| A46B 11/00 | (2006.01) |
| A46B 9/04  | (2006.01) |
| A46B 9/02  | (2006.01) |

(52) U.S. Cl.
CPC ............ *A46B 9/04* (2013.01); *A46B 9/026* (2013.01); *A46B 11/002* (2013.01); *A46B 11/0041* (2013.01); *A61C 15/00* (2013.01); *A46B 2200/108* (2013.01)

(58) Field of Classification Search
CPC ............ A46B 11/001; A46B 11/0013; A46B 11/0041; A61C 15/00
USPC ........................... 401/278, 284, 286
See application file for complete search history.

(56) References Cited

FOREIGN PATENT DOCUMENTS

| KR | 10-2004-0008970 | 1/2004  |
| KR | 10-0468075      | 1/2005  |
| KR | 10-2006-0119870 | 11/2006 |
| KR | 20-0465554      | 2/2013  |

OTHER PUBLICATIONS

English Translation of 10-2004-0008970.
English Translation of 10-2006-0119870.
English Translation of 20-0465554.
English Translation of 10-0468075.

*Primary Examiner* — David Walczak
*Assistant Examiner* — Joshua Wiljanen
(74) *Attorney, Agent, or Firm* — KORUS Patent, LLC; Seong Il Jeong

(57) ABSTRACT

According to the portable interdental toothbrush in accordance with to the present invention, when the interdental toothbrush is carried without using it, the cleaning solution is not discharged since the elastic ball disposed on the assembly protrusion of the cleaning solution tube is closely adhered to the outflow grooves and passing grooves, and, when it is used, the cleaning solution is discharged through the discharge hole, passes through the passing grooves, and reaches the brush since the elastic ball is separated and apart from the outflow grooves, whereby it is convenient to use and carry, it has a simple structure to enable mass production at a low cost, and it allows any user to use which promotes the dental and oral health for citizens.

7 Claims, 13 Drawing Sheets

PORTABLE INTERDENTAL TOOTHBRUSH

CROSS-REFERENCE TO RELATED APPLICATION(S)

This application claims the benefit of International Application No. PCT/KR2014/006487, filed on Jul. 17, 2014, based on Korean Patent Application No. 10-2014-0090113, filed on Jul. 17, 2014, the disclosure of which is hereby incorporated by reference herein in its entirety.

BACKGROUND

1. Technical Field

The present invention relates to a portable interdental toothbrush and is more particularly concerned with a portable interdental toothbrush in which a user can carry for portable use during travel or outing so as to clean and sterilize foreign materials and plaque that fit between teeth after meals; the discharge of a cleaning solution is controlled by opening and closing the outflow grooves and the passing grooves while contracting and expanding operations of the elastic ball placed on an assembly prolusion of a cleaning solution tube easily supplying the cleaning solution to the toothbrush in a state where the interdental toothbrush is carried; its use is convenient, the structure becomes simple, and manufacturing cost is low.

2. Description of the Related Art

In general, the interdental toothbrush has mull brush-shaped bristles for cleaning spaces between the teeth mounted on the end of the handle. They are orally hygiene instruments used to clean the oral cavity by washing interdental spaces using putting in and pulling out motions of the brush in the interdental space gaps. Use of the interdental toothbrush facilitates removal of food-residue and plaque of hard-to-reach areas of usual toothbrushes, sterilization after dental treatment such as scaling, prevention of plaque after smoking, and cleaning of orthodontic instruments such as braces to maintain oral hygiene.

However, looking at the actual state of use of the current interdental brush there are problems that the cleaning is conducted only using the brush and thus gums become stimulated bleeding occurs frequently and the ability to remove food-residue and plaque becomes insufficient. Further, if interdental brushes are continuously used, there is an unpleasant smell from the brush due to a bad cleanliness, particularly, the growth of bacteria.

In an attempt to solve the above-mentioned problems, as shown in FIG. 1, there has been developed toothbrush in which a lid 120 containing a cleaning solution 140 is coupled inside the toothbrush 110 coupled with bristles 130, and each time the user uses it, the toothbrush 110 is immersed in the cleaning solution so that the toothbrush 110 is soaked with the cleaning solution 130. However, this method has disadvantages in that the cleaning solution 140 is stored in the lid 120 of the toothbrush 110 and thus the cleaning solution can be discharged outside if the lid 120 is open due to the uses carelessness. Also, care should be taken for preventing loss of the cleaning solution stored in the lid 120 when using the toothbrush 110. Further, it is troublesome to repeat the motions of putting, in and pulling out the toothbrush 110 in the lid 120 every time the user tries to soak the toothbrush 110 in the cleaning solution.

To solve the above problems, Korean Patent No. 10-0468075 titled "An interdental toothbrush provided with a cleaning solution" has been suggested. The interdental toothbrush disclosed in this patent comprises, as shown in FIG. 2, a case 40 having both ends opened, a storage tank 30 installed in the case 40, on one side of which is formed a discharge hole 32, and the other side of which is open, a pleated tube 70 coupled to the opened outer circumferential face of the storage tank 30 and to a check valve 80 joined to an end thereof, a spring 55 installed on the outer circumferential face of the discharge hole 32, a coupling socket 50 installed on the outer circumferential face of the discharge hole 32 and having a screw part on the outer circumferential face thereof, a nozzle 60 screw-coupled to the discharge hole 32, an end portion of which is split into upper and lower parts, and having a cone-shaped discharge hole inside and a slanted bump 62 on an outer circumferential face thereof, a fixing ring 65 coupled to the split outer circumferential face of the nozzle 60 and contacted with a side surface of the coupling socket 50, and a nozzle cap 90 engaged in the screw portion formed on the coupling socket 50 and having a brush 95 assembled on the front surface thereof and a couple of injection holes 92 formed therein. This interdental toothbrush is effective in eliminating the inconvenience of handling cleaning solution of the prior art, however, the structure is complicated and the manufacturing cost is high, so it is not practical. Further, when the cleaning solution is all used up, the storage tank 30 should be replenished with a new cleaning solution, however, it is impossible to replenish the cleaning solution in the storage tank 30, which makes it impossible to continuously use the interdental toothbrush purchased at a high price.

SUMMARY

It is an object of the present invention to solve the above-described problems encountered with the prior arts and to provide a portable interdental toothbrush which is capable of conveniently carrying it and ensuring its activity since the cleaning solution is received in a state of being sealed tightly; when using the interdental toothbrush, the discharge of a cleaning solution can be easily controlled by tightening and releasing an elastic ball with contracting and expanding operations of the elastic ball disposed on a tip of a cleaning solution tube; its structure is simple; manufacturing cost is low, and its use is convenient.

The above objects of the present invention is achieved by a portable interdental toothbrush according to the present invention comprising: a cleaning solution tube in which a cleaning solution is received to carry it conveniently and an assembly protrusion is formed for controlling the discharge of the cleaning solution with an elastic ball disposed on a tip thereof; and a brush body in which a brush is fixed to a tip, a plurality of passing grooves are formed on the periphery of the brush on the tip to which the brush is fixed, and an assembly move hole is formed on a bottom surface in a lower part of the tip of the cleaning solution tube to which an elastic ball is assembled, wherein discharge of the cleaning solution is controlled by the operation in which the assembly protrusion of the cleaning solution tube moves forward and backward to contract and expand the elastic ball to close and open the outflow grooves and passing grooves.

According to the portable interdental toothbrush in accordance with to the present invention, when the interdental toothbrush is carried without using it, the cleaning solution is not discharged since the elastic ball disposed on the assembly protrusion of the cleaning solution tube is closely adhered to the outflow grooves and passing grooves, and, when it is used, the cleaning solution is discharged through the discharge hole, passes through the passing grooves, and reaches the brush since the elastic ball is separated and apart from the outflow grooves, whereby it is convenient to use and carry, it has a simple structure to enable mass production at a low cost, and it allows any user to use, which promotes the dental and oral health for citizens.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Figure 1:
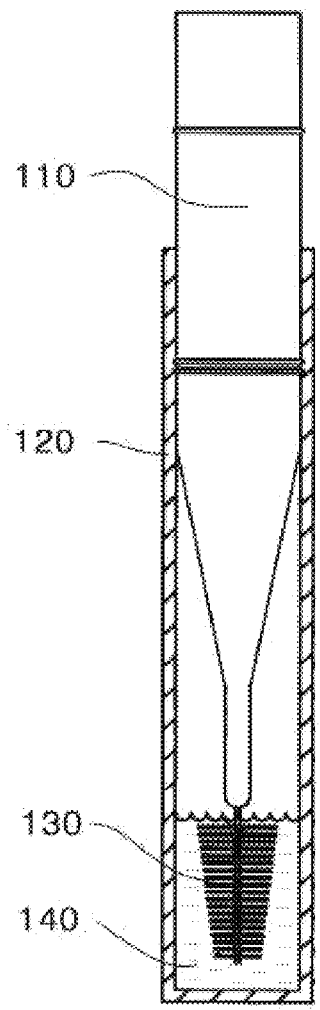
FIG. 1 is a longitudinal cross-sectional view of a conventional interdental toothbrush.
Figure 2:
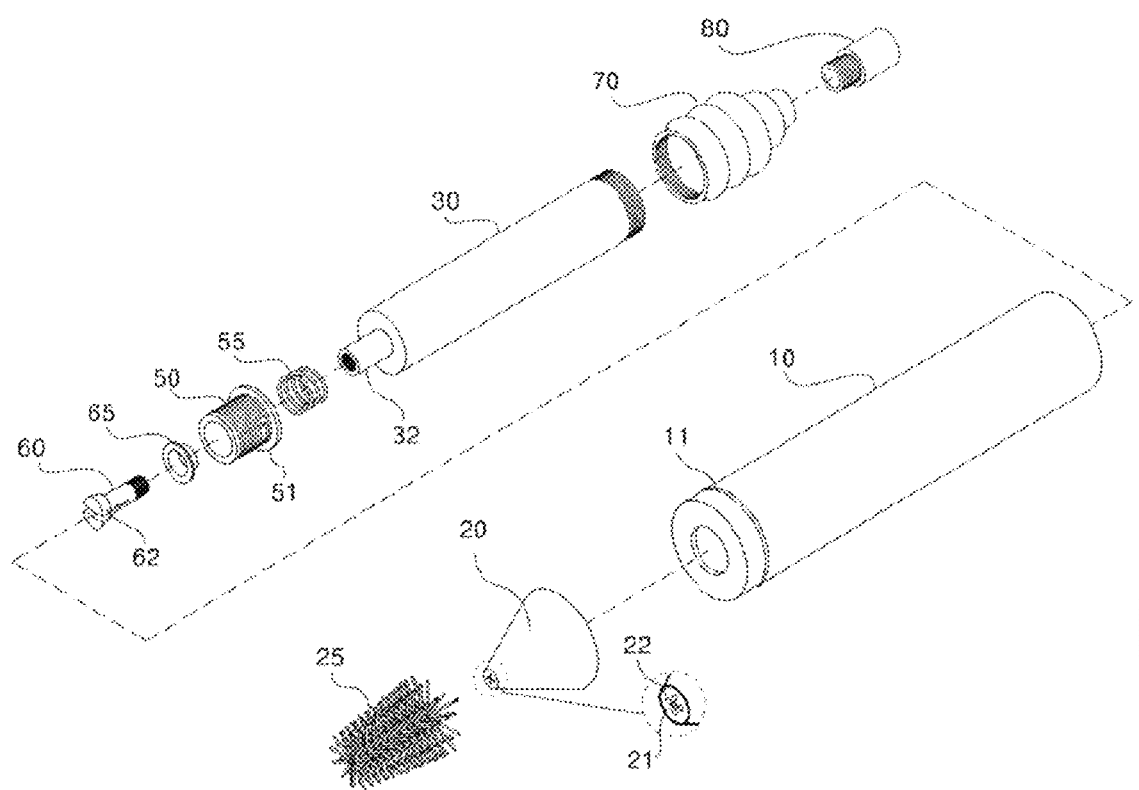
FIG. 2 is an exploded perspective view of another conventional interdental brush.

Hereinafter, the configuration and operation of preferred embodiments of the present invention will be described in detail with reference to the accompanying drawings. Here, in the case of assigning the reference numerals to the components of the drawings, it should be noted that, with respect to the same components, the same reference numerals are used even in different drawings.

Figure 3:
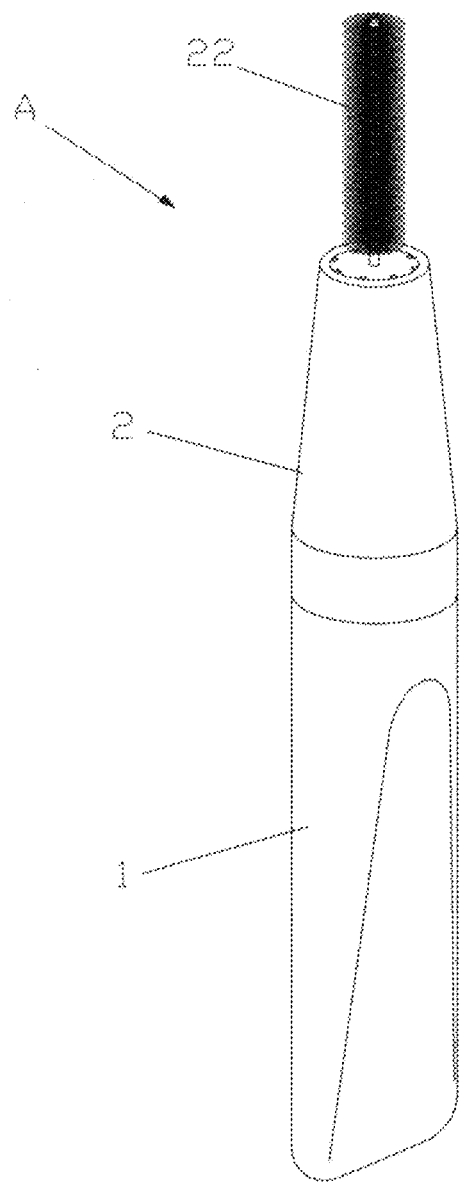
FIG. 3 is a perspective view of a portable interdental toothbrush in accordance with the first embodiment of the present invention.
Figure 4:
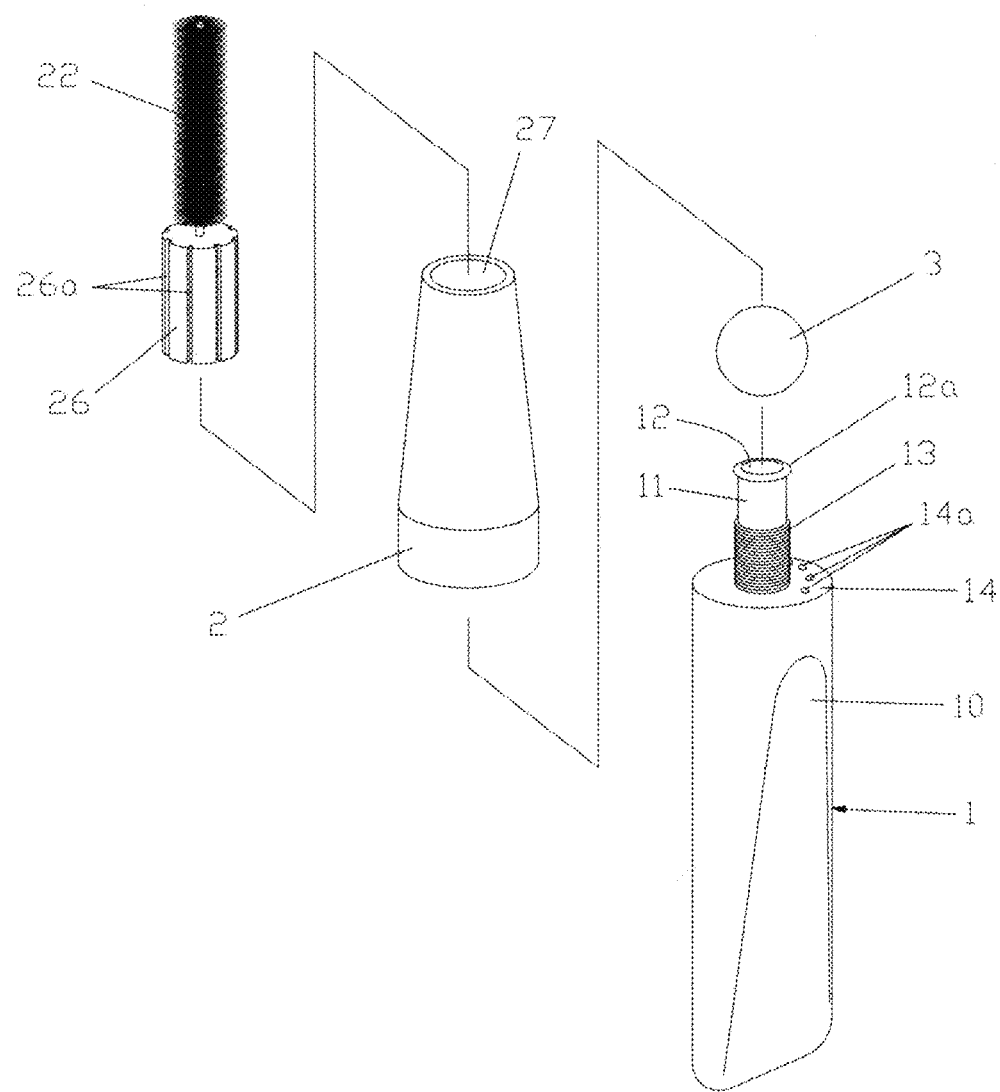
FIG. 4 is an exploded perspective view of a portable interdental toothbrush in accordance with the first embodiment of the present invention.
Figure 5:
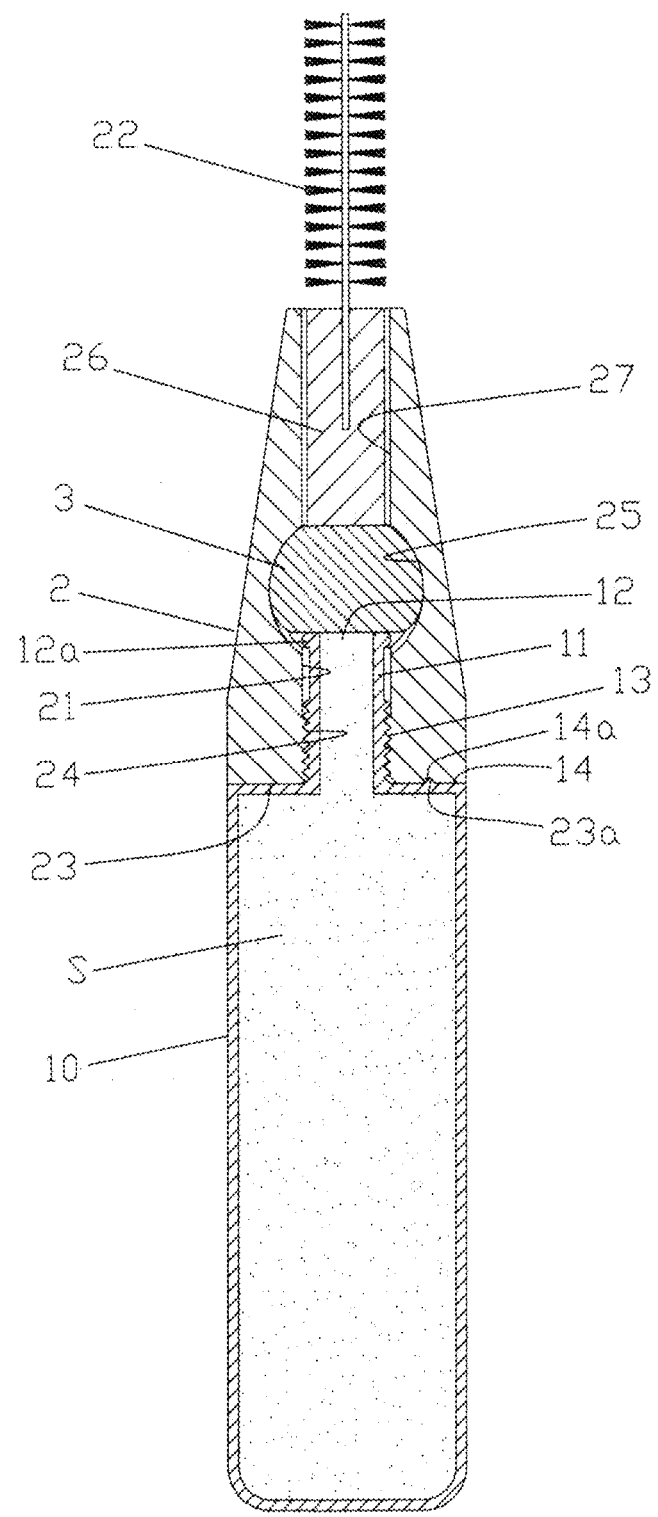
FIG. 5 is a schematic longitudinal cross-sectional view of a portable interdental toothbrush in accordance with the first embodiment of the present invention.

As shown in FIGS. 3, 4 and 5, a portable interdental toothbrush A according to the first embodiment of the present invention comprises: a bottle-shaped cleaning solution tube 1 receiving a cleaning solution S containing fluorine; a brush assembly 2 in which an assembly groove hole 21 for a bottleneck portion of the cleaning solution tube 1 to be inserted and assembled is formed on one end and a brush 22 is fixed to the other end; and an elastic ball 3 which can be expanded and contracted and is disposed on a tip of the cleaning solution tube 1 inside the brush assembly 2.

The cleaning solution tube 1 is made of synthetic resins to make its manufacturing convenient, and comprises, as shown in FIGS. 3, 4 and 5, a tube body 10 in which a cleaning solution S is received, an assembly protrusion 11 protruded with a smaller diameter than that of the tube body 10, in which a discharge hole 12 for being equivalent to a bottleneck portion extended from the tube body 10 with a smaller diameter than that of the tube body 10 and discharging, the cleaning solution S is formed on a tip and an assembly screw portion 13 is formed outside a lower portion, and an engaging protrusion 14 formed on a severed portion between the tube body 10 and the assembly protrusion 11. On both sides of the tube body 10, planar portions are formed to attach labels or advertisements.

In order to prevent damage, reinforced rim 12a is formed thickly on the tip in which the discharge hole 12 of the assembly protrusion 51 is formed, thus reinforcing the strength of the discharge hole.

A plurality of protrusions 14a are formed on the engaging protrusion 14, positions of the protrusions 14a are different, and the assembled state with the brush assembly 2 is varied depending on the positions of the protrusions 14a, thereby identifying the assembled state with the brush assembly 2 easily.

In the brush assembly 2, the brush 22 is fixed to one end and the assembly move hole 21 is formed on the other end. On a bottom surface 23 contacting the engaging protrusion 14 of the assembly groove hole 21, insertion grooves 23a for engaging protrusions 14a with each other and inserting the protrusions 14a are formed.

A negative screw portion 24 for engaging the assembly screw portion 13 is formed inside the lower part of the assembly groove hole 21 to be assembled with the cleaning solution tube 1.

A plurality of outflow grooves 25a are formed in a longitudinal direction on an inner wall of a middle space 25, which is located in the middle of the assembly groove hole 21 and in which the elastic ball 3 is inserted, whereby the cleaning solution S discharged through the discharge hole 12 of the cleaning solution tube 1 is discharged along the outflow mows 25a Discharge of the cleaning solution S is controlled in the following way. If the cleaning solution tube 1 is rotated in an opening direction in a state where the cleaning solution tube 1 and the brush assembly 2 are screw-coupled, more cleaning solution is discharged through the outflow grooves 25a. If the cleaning solution tube 1 is rotated in a tightening direction, then the elastic ball 3 is pressed and the outflow grooves 25a are pressed. This prevents the cleaning solution from passing through the outflow grooves 25a, thereby stopping the discharge of the cleaning solution S.

To fix the brush 22 to the brush assembly 2, a plurality of passing grooves 26a are formed in a longitudinal direction on an outer surface of the fixing rod 26 fixed on one end of the brush 22, and the fixing rod 26 is inserted and fixed into the brush fixing hole 27 formed on one end of the brush assembly 2, thereby fixing the brush 22 to the brush assembly 2. As an alternative example, a method in which a cylindrical fixing rod 26 fixing the brush 22 on one end is inserted into the brush fixing hole 27 on an inner surface of which are formed a plurality of passing grooves to form passing grooves is included apparently within the scope of the present invention.

Once the brush 22 is fixed to the brush assembly 2, the cleaning solution S is supplied to the brush 22 through the discharge hole 12 of the cleaning solution tube 1, outflow grooves 25a of the middle space 25 of the brush assembly 2, and the passing grooves 26a of the brush assembly 2.

The elastic ball 3 is inserted in the middle space 25 of the brush assembly 2, the lower part of which is in contact with the tip on which the discharge hole 12 of the assembly protrusion 11 of the cleaning solution tube 1 is formed, and the side surface and the upper part of which are in contact with the middle space 25 of the assembly 2, which becomes an important element fix controlling discharge of the cleaning solution S.

Figure 6A:
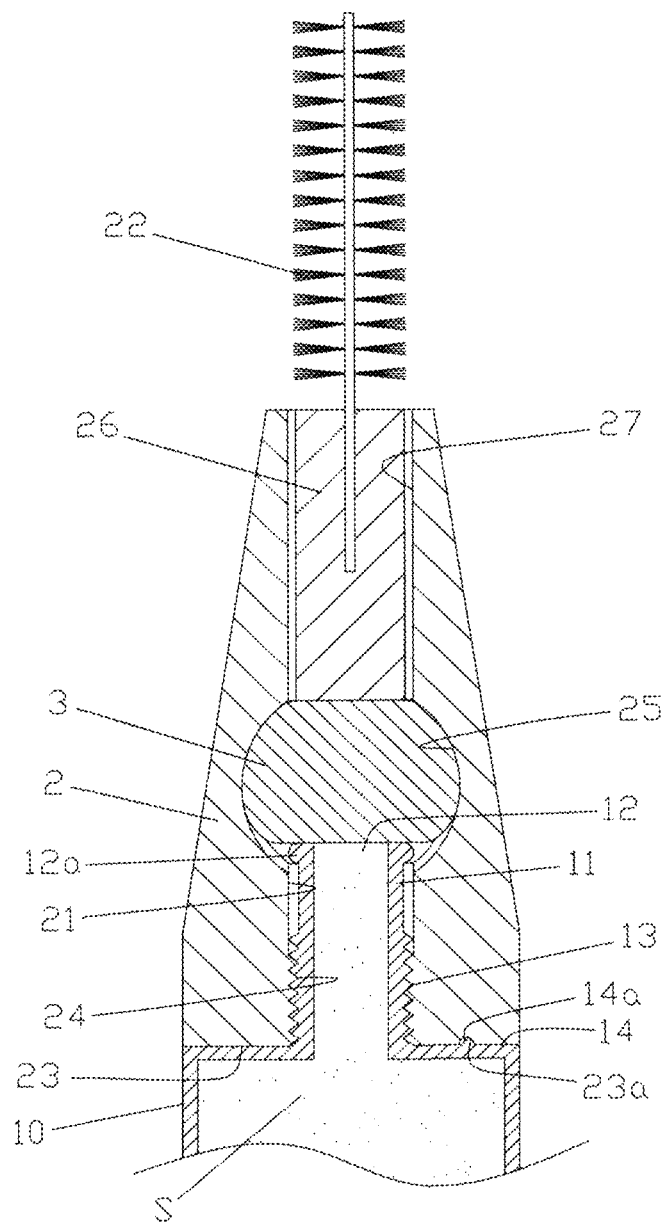
FIGS. 6a and 6b are longitudinal and horizontal cross-sectional views of a portable interdental toothbrush in accordance with the first embodiment of the present invention when the elastic ball is contracted.
Figure 6B:
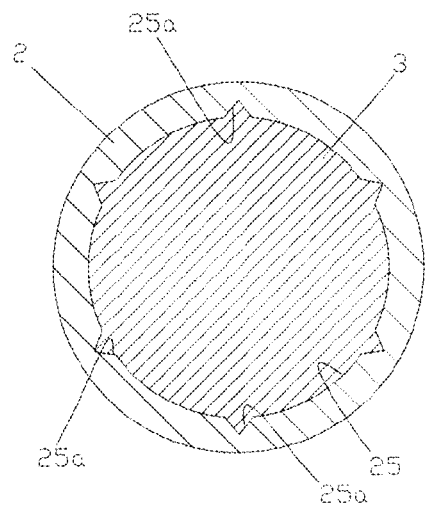

That is, discharge control of the cleaning solution S is performed in the following way, lithe cleaning solution tube 1 is rotated in an opening direction in a state where the cleaning solution tube 1, the elastic ball 3, and the brush assembly 2 are screw-coupled, more cleaning solution is discharged through the outflow grooves 25a of the middle space 25 since the elastic ball 3 and the middle space 25 are not pressed (See FIGS. 7a and 7b). If the cleaning solution tribe 1 is rotated in a tightening direction, then the tip on which the discharge hole 12 of the assembly protrusion 11 of the cleaning solution tube 1 is formed acts to press the elastic ball 3 and subsequently press the outflow moves 25a of the middle space 25 to close the outflow moves 25a, which prevents the cleaning solution S from passing through the outflow grooves 25a, thereby stopping the discharge of the cleaning, solution S (See FIGS. 6a and 6b).

In the present invention, the elastic ball 3 can be used, however, it is not limited thereto. Rather, a metal ball may be inserted in the middle space and moves forward and backward to open and close the passing grooves 26a of the brush assembly 2 to control the discharge of the cleaning solution S. Accordingly, a metal ball can be used instead of the elastic ball 3, and the elastic ball 3 and the metal ball should be construed to be identical during the interpretation of the present invention.

The operation of the portable interdental toothbrush A according to the present invention having the above configuration is described below.

Figure 7A:
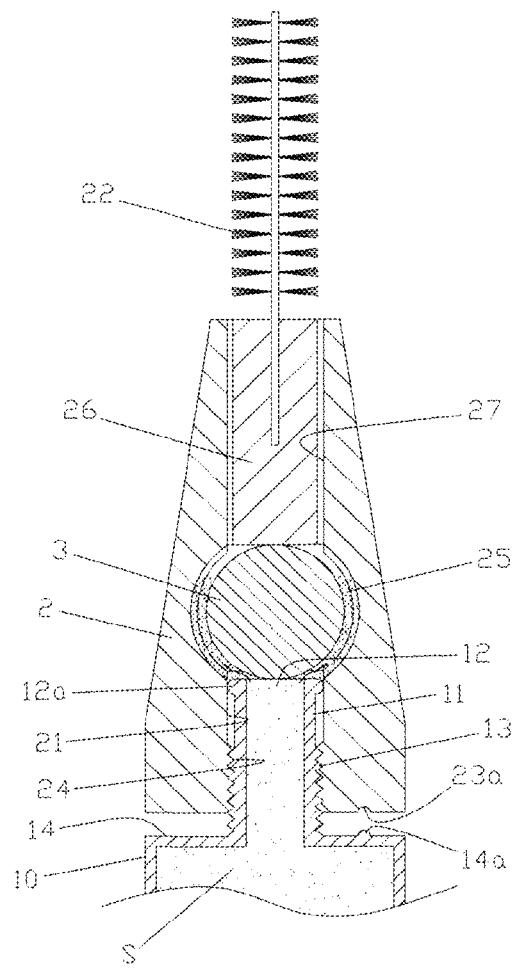
FIGS. 7a and 7b are longitudinal and horizontal cross-sectional views of a portable interdental toothbrush in accordance with the first embodiment of the present invention when the contraction of the elastic ball is released.
Figure 7B:
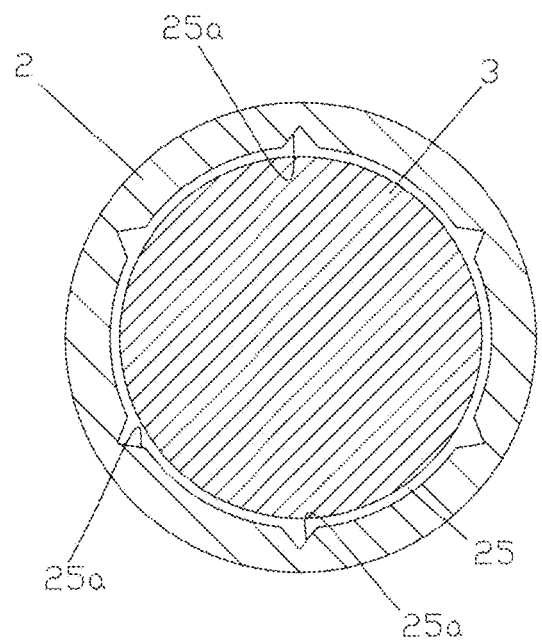
Figure 8A:
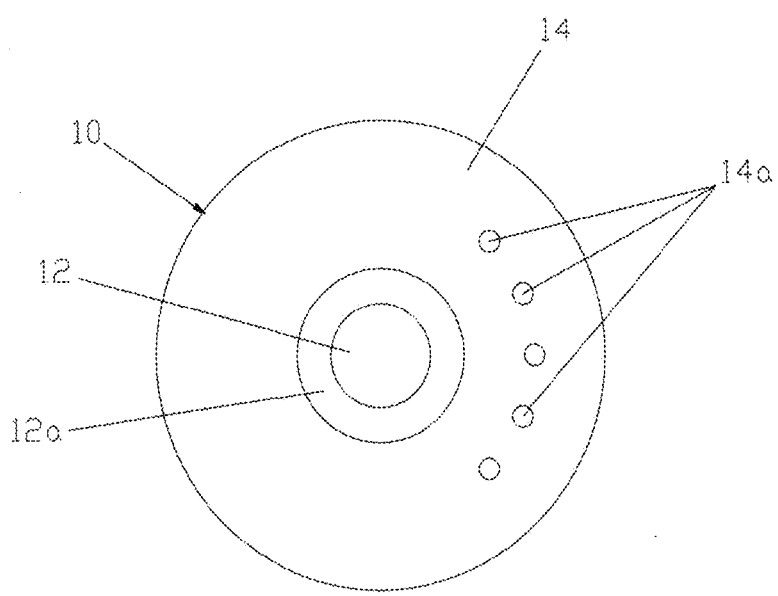
FIGS. 8a and 8b are a top view and a longitudinal cross-sectional view of an engaging protrusion portion of a portable interdental toothbrush in accordance with the first embodiment of the present invention.
Figure 8B:
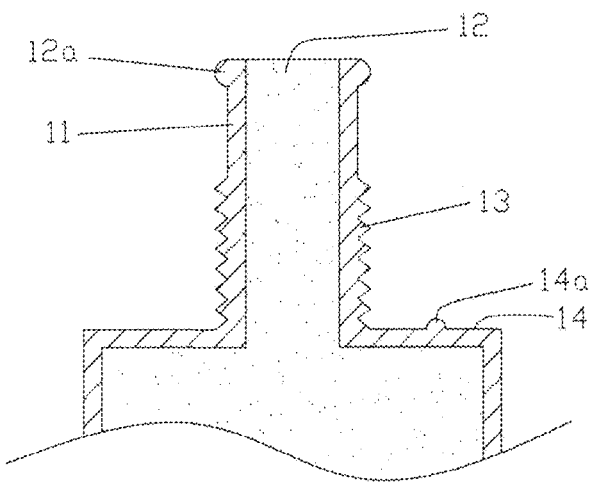

To use the portable interdental toothbrush A comprising: a bottle-shaped cleaning solution tube 1 receiving a cleaning solution S containing fluorine; a brush assembly 2 in which an assembly groove hole 21 for a bottleneck portion of the cleaning solution tube 1 to be inserted and assembled is formed on one end and a brush 22 is fixed to the other end; and an elastic ball 3 which can be expanded and contracted and is disposed on a tip of the cleaning solution tube 1 inside the brush assembly 2, if the cleaning solution tube 1 is rotated in an opening direction, since the elastic ball 3 and the middle space 25 are not pressed, the cleaning solution S is discharged through the outflow grooves 25a of the middle space 25 and supplied to the blush 22 through the passing grooves 26a of the brush assembly 2 (See FIGS. 7a and 7b). When the cleaning solution S is supplied to the brush 22 sufficiently, the cleaning solution tube 1 is rotated in a tightening direction, the tip on which the discharge hole 12 of the assembly protrusion 11 of the cleaning solution tube 1 is formed acts to press the elastic ball 3 and subsequently press the outflow grooves 25a of the middle space 25 to close the outflow grooves 25a, which prevents the cleaning solution S from passing through the outflow grooves 25a, and the portable interdental toothbrush A can be used in a state where discharge of the cleaning solution S is halted (See FIGS. 6a and 6b).

The extent of openness of the cleaning solution tube 1 may be conveniently recognized by the assembly of the protrusions 14a formed on the engaging protrusion 14 and the insertion groove 23a which are engaged therewith during rotation to open the cleaning solution tube 1.

If the use of the portable interdental toothbrush A is completed, the user may wash the brush 22. Then, the user may use it again conveniently as described above until the cleaning solution S is all used up.

Figure 9A:
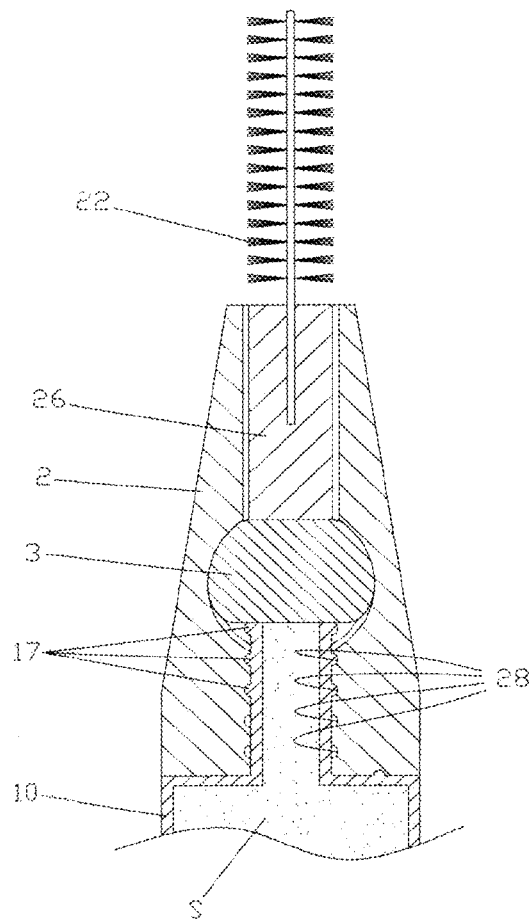
FIGS. 9a and 9b are schematic longitudinal cross-sectional views of a portable interdental toothbrush in accordance with the second embodiment of the present invention during contraction and release, respectively.
Figure 9B:
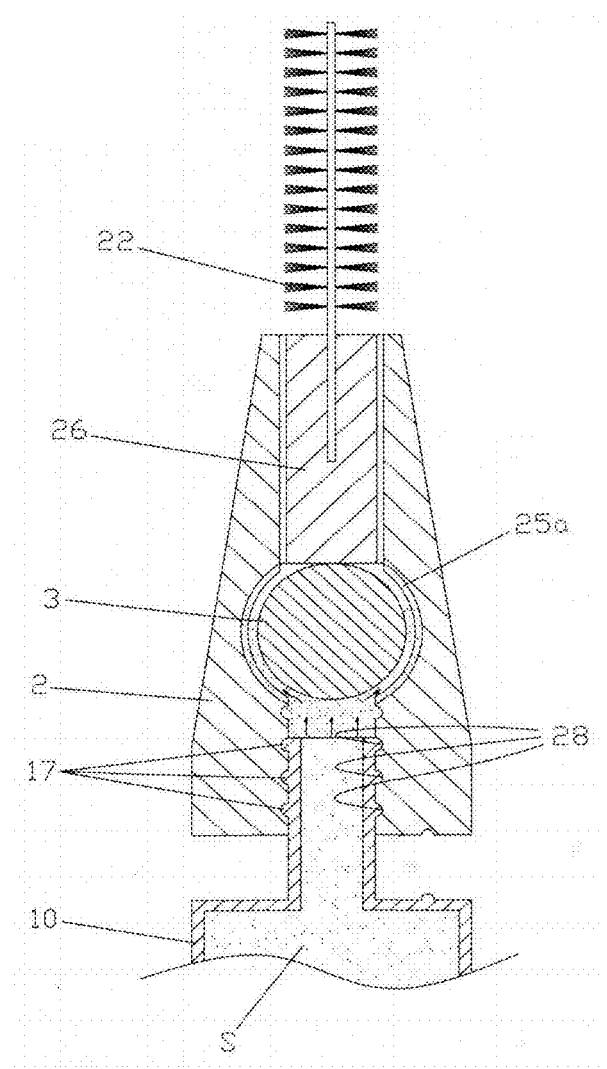

FIGS. 9a and 9b are schematic longitudinal cross-sectional, views of a portable interdental toothbrush in accordance with the second embodiment of the present invention, in which the cleaning solution tube 1 and the brush assembly 2 of the portable interdental toothbrush A are snap-assembled instead of screw-assembled, Semicircular protrusions 17 are protruded semi-circularly apart from each other at regular intervals on a side surface of the assembly protrusion 11, and corresponding insertion grooves 28 are also formed semi-circularly at corresponding regular intervals inside the assembly groove hole 21. In a state where it is not used and the cleaning solution S is not discharged, since it is assembled such that the circular protrusions 17 are engaged with the insertion grooves 28 in sequence, the elastic ball 3 is contracted and the outflow grooves 25a are pressed to close the outflow grooves 25a, whereby discharge of the cleaning solution S is stopped (See FIG. 9a). In this state, if the cleaning solution tube 1 on which the semicircular protrusions 17 are formed is pulled back to use the interdental toothbrush A, the semicircular protrusions 17 are separated from the engaged insertion grooves 28 and engaged to the lower insertion grooves 28. Accordingly, the cleaning solution tube 1 moves back to release the elastic ball 3 to return back to the original position (See FIG. 9b), which starts the discharge of the cleaning solution S to supply the cleaning solution to the brush 22.

Figure 10A:
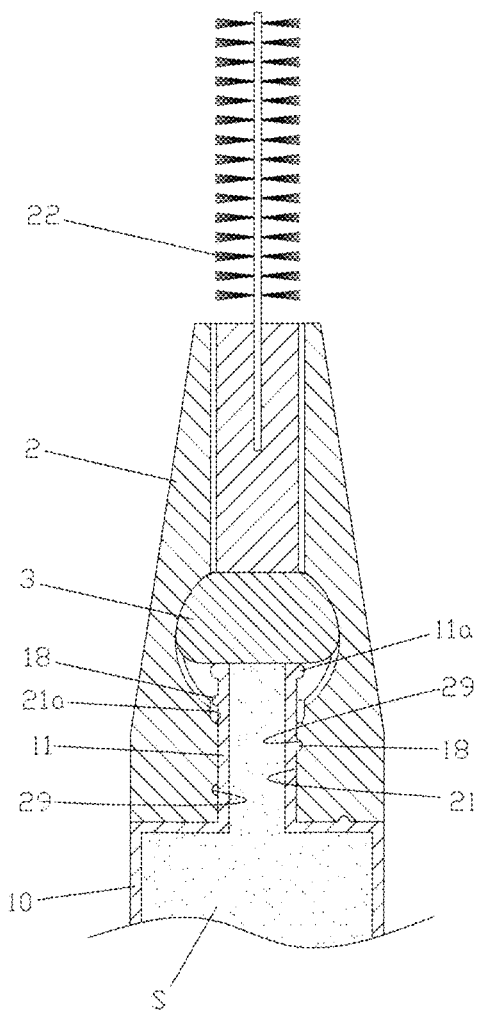
FIGS. 10a and 10b are schematic longitudinal cross-sectional views of a portable interdental toothbrush in accordance with the third embodiment of the present invention during contraction and release, respectively.
Figure 10B:
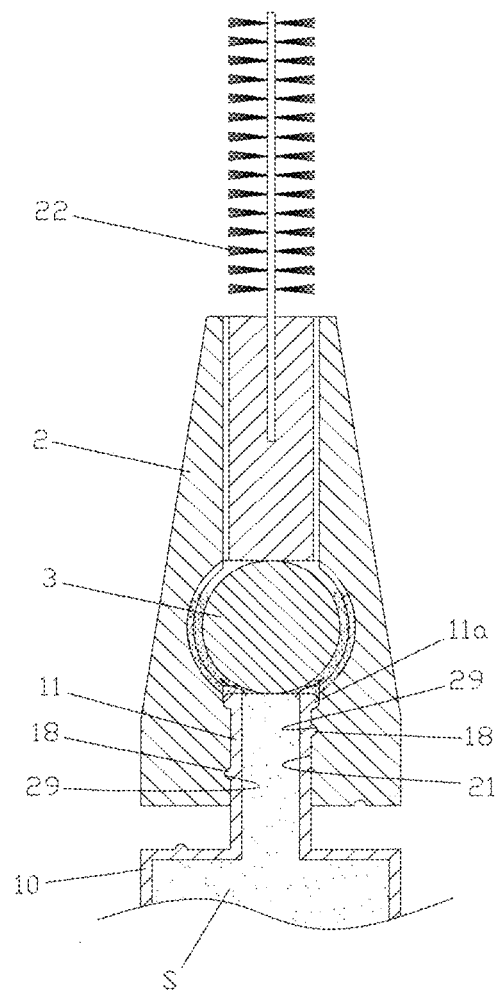

FIGS. 10a and 10b are schematic longitudinal cross-sectional dews of a portable interdental toothbrush in accordance with the third embodiment of the present invention during contraction and release, respectively, which are improved to conveniently perform the discharge and stopping of the cleaning solution. In the portable interdental toothbrush A, a protruded rim 11a for preventing backflow is formed on an upper end of the assembly protrusion 11 of the cleaning solution tube 1, a screw protrusion 18 of one or two turns is formed on a side surface of the assembly protrusion 11, a receiving groove 21a for the protruded rim 11a for preventing backflow to be settled is formed on an upper part of an inner surface of a lower end of the assembly groove hole 21 of the brush assembly 2, and a screw groove 29 of one or two turns to correspond to the screw protrusion 18 is formed on a side surface. Accordingly, if the cleaning solution tube 1 or the brush assembly 2 is rotated one or two times, it is conveniently controlled to discharge or stopping the cleaning solution, and the backflow of the cleaning solution is prevented even during slopping by the protruded rim 11a for preventing backflow.

Figure 11A:
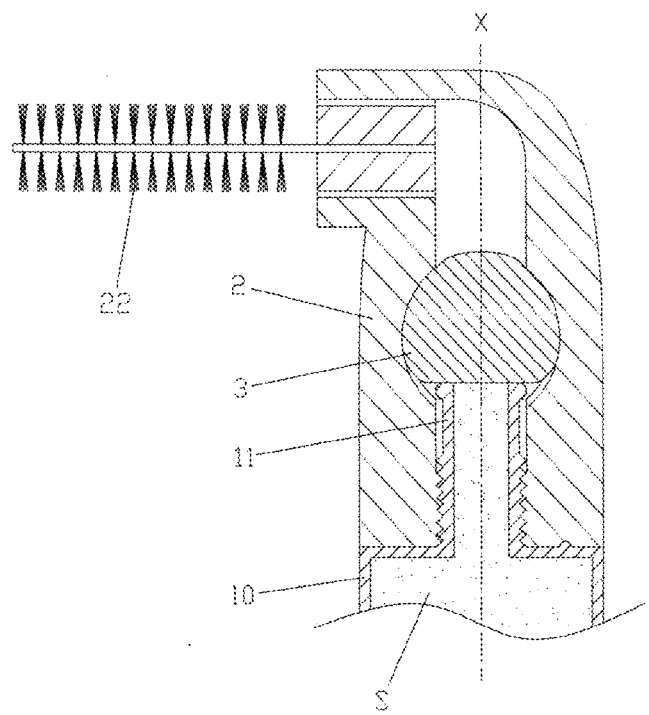
FIGS. 11a and 11b are schematic longitudinal cross-sectional views of a portable interdental toothbrush in accordance with the fourth embodiment of the present invention.
Figure 11B:
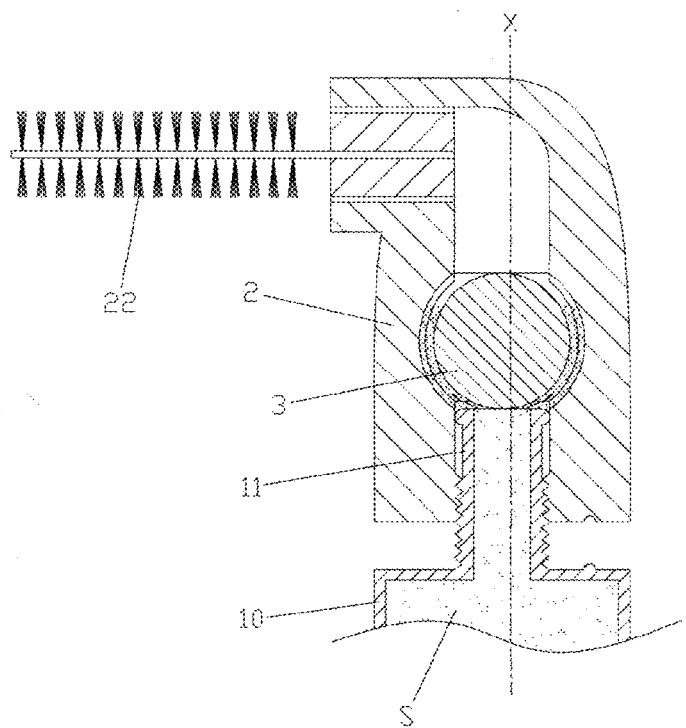

FIGS. 11a and 11b are schematic longitudinal cross-sectional views of a portable interdental toothbrush in accordance with the fourth embodiment of the present invention. The assembly structure of the brush 22 of the brush assembly 2 assembled to the assembly protrusion 11 of the cleaning solution tube 1 of the portable interdental toothbrush A is formed such that the brush fixing hole 27 is formed orthogonally to the vertical axis X for the brush 22 to cross orthogonally to the vertical axis X of the assembly groove hole 21 of the brush assembly 2, which makes the whole assembly groove hole 21 to have an angled groove of "⌐" shape. The detailed description of the structures of the cleaning solution tube 1 and the brush assembly 2 other than the above is omitted since they are the same components having the same structures and functions as those of the first embodiment of the present invention.

Since the brush 22 of the brush assembly 2 is disposed orthogonally to the vertical axis X, it may clean the tooth deep inside the oral cavity such as a molar more conveniently. Further, the cleaning solution tube 1 may be used in the orthogonal state without need to bring it up when using the interdental toothbrush A, the cleaning solution S in the cleaning solution tube 1 is prevented from flowing out more than needed, and it is possible to discharge and use the cleaning solution S as needed.

It is possible to manufacture the same products as the portable interdental toothbrush in accordance with the present invention repeatedly in the manufacturing field of the interdental toothbrush. Accordingly, the present invention possesses industrial applicability.

Although the specific embodiments of the present invention have been disclosed for illustrative purposes, those skilled in the art will appreciate that various modifications, additions and substitutions may be made to the invention without departing from the scope and spirit of the invention as disclosed in the accompanying claims.

What is claimed is:

1. A portable interdental toothbrush (A) comprising:
a bottle-shaped cleaning solution tube (1) receiving a cleaning solution (S) containing fluorine;
a brush assembly (2) in which an assembly groove hole (21) for a bottleneck portion of the cleaning solution tube (1) to be inserted and assembled is formed on one end and a brush (22) is fixed to the other end; and
an elastic ball (3) which can be expanded and contracted and is disposed on a tip of the cleaning solution tube (1) inside the brush assembly (2).

2. The portable interdental toothbrush of claim 1, wherein the cleaning solution tube (1) is made of synthetic resins to make its manufacturing convenient, and comprises: a tube body (10) in which a cleaning solution (S) is received; an assembly protrusion (11) protruded with a small diameter in which a discharge hole (12) for being equivalent to a bottleneck portion extended from the tube body (10) with a small diameter and discharging the cleaning solution (S) is formed on a tip and an assembly screw portion (13) is formed outside a lower portion; and an engaging protrusion (14) formed on a severed portion between the tube body (10) and the assembly protrusion (11).

3. The portable interdental toothbrush of claim 1, wherein, in the brush assembly (2), the brush (22) is fixed on one end and the assembly groove hole (21) is formed on the other end, a negative screw portion (24) for engaging with assembly screw portion (13) is formed inside of a lower part of the assembly groove hole (21), a plurality of outflow grooves (25a) are formed in a longitudinal direction on an inner wall of a middle space (25), which is located in the middle of the assembly groove hole (21) and in which an elastic ball (3) is inserted, a brush fixing hole (27) into which a fixing rod (26) fixed on one end of the brush (22) is inserted and fixed is formed in the upper portion of the middle space (25).

4. The portable interdental toothbrush of claim 3, wherein a plurality of passing grooves (26a) are formed in a longitudinal direction on an outer surface of the fixing rod (26) fixed on one end of the brush (22), and the fixing rod (26) is inserted and fixed into the brush fixing hole (27) formed on one end of the brush assembly (2) to form the passing grooves (26a) through which the cleaning solution passes.

5. A portable interdental toothbrush (A) comprising:
a bottle-shaped cleaning solution tube (1) receiving a cleaning solution (S) containing fluorine;
a brush assembly (2) in which an assembly groove hole (21) for a bottleneck portion of the cleaning solution tube (1) to be inserted and assembled is formed on one end and a brush (22) is fixed to the other end; and
an elastic ball (3) which can be expanded and contracted and is disposed on a tip of the cleaning solution tube (1) inside the brush assembly (2), wherein:
the cleaning solution tube (1) is made of synthetic resins to make its manufacturing convenient, and comprises a tube body (10) in which a cleaning solution (S) is received; and an assembly protrusion (11) protruded with a smaller diameter than that of the cleaning solution tube (1), in which a discharge hole (12) for being equivalent to a bottleneck portion extended from the tube body (10) with a small diameter and discharging the cleaning solution (S) is formed on a tip and a plurality of semicircular protrusions (17) apart from each other circularly are formed protruded outside a lower portion; and,
in the brush assembly (2), the brush (22) is fixed on one end, and the assembly groove hole (21) is formed on the other end, and insertion grooves (27) apart from each other to correspond to the semicircular protrusions (17) are formed circularly inside the lower part of the assembly groove hole (21) to be snap-assembled to the semicircular protrusions (17).

6. A potable interdental toothbrush (A) comprising:
a bottle-shaped cleaning solution tube (1) receiving a cleaning solution (S) containing fluorine;
a brush assembly (2) in which an assembly groove hole (21) for a bottleneck portion of the cleaning solution tube (1) to be inserted and assembled is formed on one end and a brush (22) is fixed to the other end; and
an elastic bell (3) which can be expanded and contracted and is disposed on a tip of the cleaning solution tube (1) inside the brush assembly (2), wherein:
the cleaning solution tube (1) is made of synthetic resins to make its manufacturing convenient, and comprises a tube body (10) in which a cleaning solution (S) is received; and an assembly protrusion (11) protruded with a smaller diameter than that of the cleaning solution tube (1), in which a discharge hole (12) for being equivalent to a bottleneck portion extended from the tube body (10) with a small diameter and discharging the cleaning solution (S) is formed on a tip and a screw protrusion (18) of one or two turns is formed on a side portion, and,
in the brush assembly (2), the brush (22) is fixed on one end, and the assembly groove hole (21) is formed on the other end, and a screw groove (29) of one or two turns to correspond to the screw protrusion (18) is formed inside of the lower part of the assembly groove hole (21).

7. The portable interdental toothbrush of claim 6, wherein a protruded rim (11a) for preventing backflow is formed in an upper part of the assembly protrusion (11) and a receiving groove (21a) for the protruded rim (11a) for preventing backflow is formed on an upper part of an inner surface of a lower end of the assembly groove hole (21) of the brush assembly (2).

* * * * *